United States Patent [19]

Elliott

[11] Patent Number: 4,800,899

[45] Date of Patent: Jan. 31, 1989

[54] APPARATUS FOR DESTROYING CELLS IN TUMORS AND THE LIKE

[75] Inventor: Martin K. Elliott, Milpitas, Calif.

[73] Assignee: Microthermia Technology, Inc., Mountain View, Calif.

[21] Appl. No.: 924,656

[22] Filed: Oct. 29, 1986

Related U.S. Application Data

[63] Continuation-in-part of Ser. No. 663,743, Oct. 22, 1984, abandoned.

[51] Int. Cl.$^4$ .............................................. A61N 1/06
[52] U.S. Cl. ..................................... 128/804; 128/736; 128/401
[58] Field of Search ............... 128/783, 784, 804, 665, 128/642, 401

[56] References Cited

U.S. PATENT DOCUMENTS

| 2,032,859 | 3/1936 | Wappler | 128/784 |
| 3,077,195 | 2/1963 | Fölsche | 128/804 |
| 4,311,154 | 1/1982 | Sterzer et al. | 128/804 |
| 4,448,198 | 5/1984 | Turner | 128/804 |
| 4,612,940 | 9/1986 | Kasenich et al. | 128/804 |
| 4,643,186 | 2/1987 | Rosess et al. | 128/784 |
| 4,658,836 | 4/1987 | Turner | 128/804 |
| 4,662,383 | 5/1987 | Sogawa et al. | 128/784 |
| 4,676,258 | 6/1987 | Inokuchi et al. | 128/804 |

FOREIGN PATENT DOCUMENTS

| 131389 | 5/1932 | Austria | 128/784 |
| 2929223 | 10/1980 | Fed. Rep. of Germany | 128/784 |
| 718993 | 1/1932 | France | 128/804 |
| 889010 | 12/1981 | U.S.S.R. | 128/804 |
| 249605 | 3/1926 | United Kingdom | 128/804 |
| 826646 | 3/1961 | United Kingdom | 128/804 |

OTHER PUBLICATIONS

"Electromagnetic Syringe" by Taylor; IEEE Trans on Biomed. Eng. vol. 25 No. 3 May 1978 pp. 303-304.
"Increasing Electromagnetic energy Transmission ..." by Diag. et al.; Med. & Biol. Eng. & Comput. vol. 25 May 1987 pp. 347-349.
"Microwave Applicators For Localized Hyperthermia ..." by Poglione et al., Int. Microwave Symp. Digest; 28-30 May 1980 Wash., D.C. pp. 351-354.

Primary Examiner—Lee S. Cohen
Attorney, Agent, or Firm—Townsend & Townsend

[57] ABSTRACT

Apparatus and a method for applying electromagnetic energy to the interior of a tumor, such as a breast tumor or brain tumor within the body, to heat and thereby destroy cells in the tumor while monitoring the temperature of the body tissues at the outer periphery of tumor. The energy is radiated from an antenna in the form similar to a hypodermic needle which is inserted into the body and into the tumor, the energy being supplied by a microwave generator which can be controlled as to time of operation and power output to the antenna. A temperature sensor or sensors are also inserted in the body and are located at the outer periphery of the tumor. The sensors are coupled with a temperature detector and a control unit which controls the operation of the microwave generator to actuate and deactuate it in accordance with the temperature at the outer periphery of the tumor. The video system is used to assist in placing the antenna and the temperature sensor at the proper location with reference to the tumor within the body. The present invention is especially suitable for use in destroying cancerous tumors of the breast, brain, skin or other body locations as well as, in conjunction with other modalities, e.g., radiation therapy, chemotherapy and the like, as they increase in tissue temperature enhances the efficacy of the therapy.

3 Claims, 2 Drawing Sheets

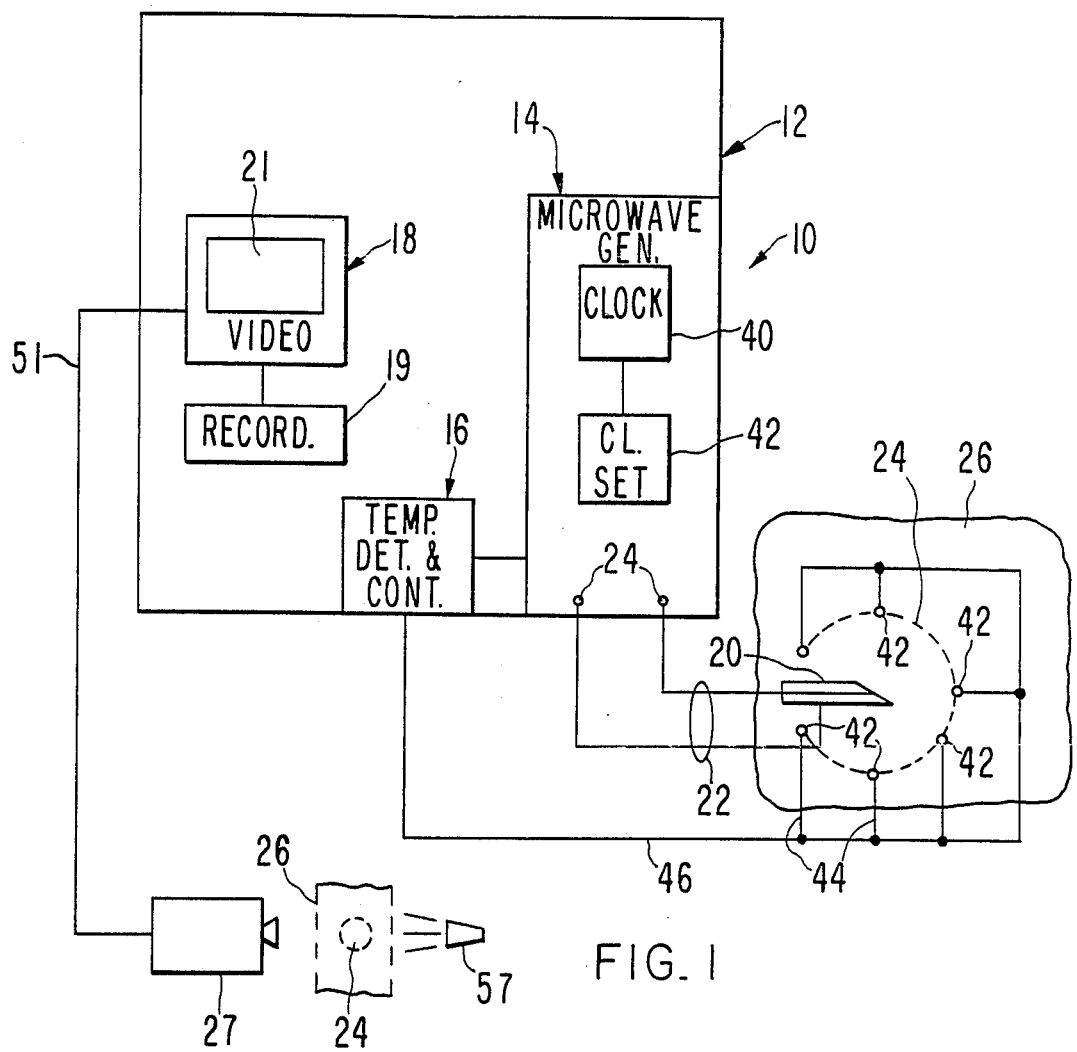
FIG. 1
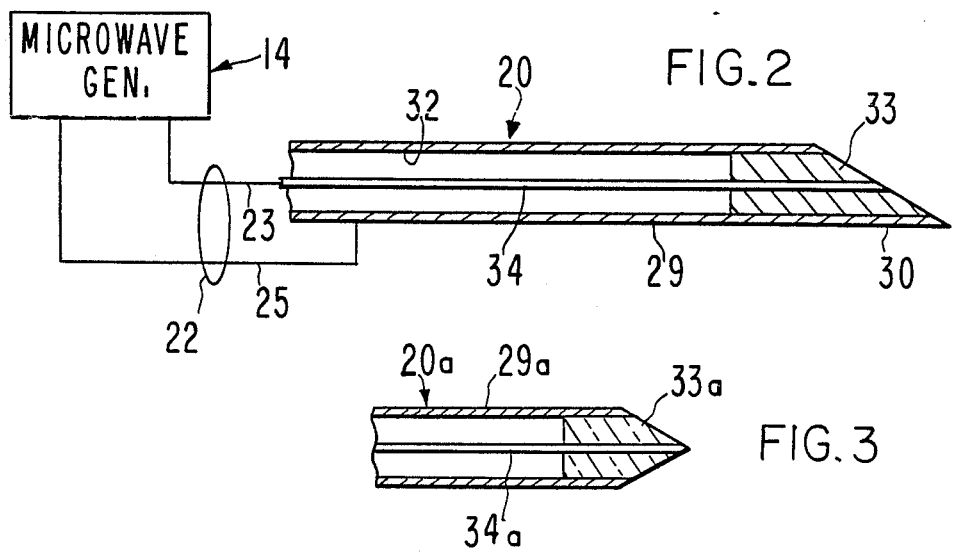
FIG. 2
FIG. 3

APPARATUS FOR DESTROYING CELLS IN TUMORS AND THE LIKE

This is a continuation-in-part of application Ser. No. 663,743, filed Oct. 22, 1984 (now abandoned).

BACKGROUND OF THE INVENTION

This invention relates to improvements in techniques for destroying cells within the living body and, more particularly, to apparatus and a method for applying electromagnetic energy to the interior of a tumor within the body to destroy cells in the tumor.

Hyperthermia, the heating of the body cells to above 41° C. for therapeutic purposes, particularly to destroy cancer tumors, has been known and used in the past. It is also known, that, above 46° C., irreversible destruction of healthy and diseased body cells occurs. The purpose of hyperthermia equipment generally is to deliver heat preferentially to diseased body cells while maintaining adjacent healthy cells at acceptable temperatures, i.e., below the temperature at which irreversible cell destruction occurs.

There are three main theories which explain why hyperthermia is successful in fighting cancerous growths. Some scientists believe that heat produces a localized fever which causes lymphocytes to congregate (200 lymphocytes are usually needed to destroy one cancerous cell). Other scientists think heat improves the flow of blood in the tumor, and this increased blood flow, in turn, brings more oxygen to the tumor and lowers its PH, thus starving the tumor cells by reducing nutrients. A third theory contends that the DNA forces that hold tumorous cells together are weaker than those of healthy cells and the heat applied to the tumorous cells breaks them apart and thereby destroys them more easily.

A number of disclosures relating to the method of treating tumors by the application of electromagnetic radiation to the tumors include U.S. Pat. Nos. 3,991,770, 4,032,860, 4,095,602, 4,119,102, 4,154,246, 4,230,129, 4,346,715 and 4,397,314. Another disclosure relating to surgical instruments in the form of an electrically heated hypodermic needle is U.S. Pat. No. 3,698,394.

A commercial system for producing deep controlled regional hyperthermia has been made and sold by BSD Medical Corporation, 420 Chipeta Way, Salt Lake City, Utah 84108. The system uses the principle of phase reinforcement to create an electrical field within the human body that produces heat internally. A number of radiating elements surround the patient and direct radio frequency (RF) energy through the treatment area in the applicator field. Thus, the sources of electromagnetic energy for the area to be treated in the patient are external to the patient.

A technique of treating brain tumors by microwave energy has been disclosed in an article entitled, "Brain Tumors Succumb to New Microwave Probes," in Microwave Technology, June 19, 1983. In this technique, a hole is drilled into the skull and a catheter is invasively inserted in the hole to support a coaxial radiator or antenna. Microwave energy is then applied to the antenna to cause the brain tumor to be heated to the point at which cancerous cells in the tumor are destroyed.

The foregoing disclosures relate to hyperthermia equipment which is complex in construction, expensive to produce and maintain, and requires a considerable volume of space to accommodate the relatively large size of such equipment. Because of these drawbacks, a need has arisen for improved hyperthermia equipment and techniques which simplifies the way internal body tumors are treated, for example, tumors of the breast. The present invention satisfies this need.

SUMMARY OF THE INVENTION

The present invention comprises apparatus and a method for applying heat energy to the interior of a tumor or other body part located on or within the living body. The heat is applied within the tumor or body part without excessively heating healthy cells surrounding the tumor or body part.

The apparatus includes an antenna which is constructed in the form of a hypodermic needle which can be inserted through the skin and into the tumor with minimal discomfort to the patient. The antenna may be sufficiently small in diameter so as to be minimally invasive in the medical sense. It is coupled by way of a coaxial cable to a microwave generator in a housing or other support structure adjacent to a patient treatment area. The operating time of the microwave generator can be varied so that microwave energy can be selectively applied to the tumor depending upon the condition of the tumor. A typical heating period is 20 to 40 minutes with interruptions of the applied power to the antenna when predetermined body temperatures near the outer periphery of the tumor are sensed as hereinafter described.

To assure that healthy body cells surrounding a tumor are not affected by the heat energy generated by the presence of the radiating antenna in the tumor, a plurality of temperature sensors are placed in the body at or near the outer periphery of the tumor. Each sensor is coupled to a temperature detection and control unit which monitors the temperatures at each location on the outer periphery of the tumor. If the temperature at any one location reaches a predetermined value, such as 46° C., the temperature detection and control unit will deactuate the microwave generator for a period of time sufficient to allow the temperature at the specific location to decrease to a second temperature, such as 45° C., whereupon, the microwave generator will once again be actuated. The on-off condition of the microwave generator continues until the preset heating time has elapsed. In this way, the heat energy necessary to destroy cancer cells is confined to the body region in which the tumor is located. Thus, healthy body cells are substantially kept below the temperature at which their destruction would ordinarily occur.

The apparatus of the present invention includes a video system which permits a video image of a cancerous tumor to be displayed on a video monitor. This image is formed by directing an intense light onto a body part suspected of containing a tumor. The light passing through body from the light source will present an image of a tumor if a tumor is present. This image will be sensed by a video camera and can be viewed on a video monitor. The video image on the monitor can be observed and used to assist in inserting the antenna and temperature sensors into the body and into the proper locations with respect to the tumor itself.

The apparatus of the present invention is simple and rugged in construction, is inexpensive to produce and maintain, and can be used with clinicians with minimal expertise in the operation and handling of the electronic equipment. Since the antenna has the construction of a hypodermic needle, microwave energy can readily and easily be applied to a tumor without elaborate preparation of a patient, such as by the use of local anesthesia or other procedures. Moreover, the video system of the apparatus includes a video recorder so that a record of the progress in the destruction of a cancerous tumor can be made.

The primary object of the present invention is to provide an improved apparatus and method for applying heat to the interior of a tumor within the living body wherein an antenna similar in construction to a hypodermic needle inserted into the body and into the tumor can radiate microwave energy into the tumor to heat the tumor while the temperature at the outer periphery of the tumor can be continuously monitored by sensors inserted into the body to thereby permit the destruction of cancerous cells in the tumor without destruction of healthy cells in the body surrounding the tumor.

Another object of the present invention is to provide an improved antenna for use in applying microwave energy within a tumor wherein the antenna is constructed in the form of a hypodermic needle provided with a center conductor within and spaced from an outer tubular barrel and the antenna itself can be impedance matched with human tissues and can be of a diameter less than that considered to be minimally invasive of the body to thereby allow the heating of a tumor within the body without elaborate preparation of the patient as might be required for more invasive penetration of the body.

Other objects of this invention will become apparent as the following specification progresses, reference being had to the accompanying drawing for an illustration of the invention.

In the drawing:

FIG. 1 is a schematic view of the apparatus for use in destroying tumors and other cancerous growths in the living body;

FIG. 2 is a schematic view, partly in section, of one embodiment of an antenna and a microwave generator coupled with the antenna for applying microwave energy to a tumor to heat it;

FIG. 3 is a fragmentary, cross-sectional view of another embodiment of the antenna;

Figure 4:
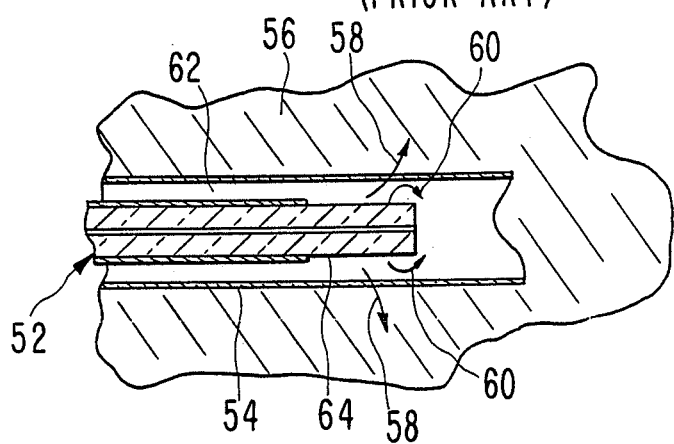
FIG. 4 is a fragmentary, cross-sectional view of a prior art coaxial cable for radiating microwave energy into human or animal tissue, the coaxial cable being in an air-filled catheter.

The apparatus of the present invention is broadly denoted by the numeral 10 and is illustrated schematically in FIG. 1. Apparatus 10 includes a housing 12 containing a number of components, including a microwave power generator 14, a temperature detector and control unit 16 and a video system 18 provided with a video recorder and playback device 19, a video monitor 21, and a video camera 27. Apparatus 10 further includes a microwave antenna 20 coupled by a coaxial cable 22 having leads 23 and 25 to power output terminals 24 of microwave generator 14. Antenna 20 is shown in more detail in FIG. 2 and will be described hereinafter.

Antenna 20 is adapted to be inserted into a tumor 24 in the living body 26 so that microwave energy can be imparted to the tumor to heat the tumor and to destroy cancerous cells therein. Temperature detection and control unit 16 is provided to sense temperatures at various locations at the outer periphery of tumor 24 and to control the actuation and deactuation of the microwave generator as a function of such temperatures.

Antenna 20 is constructed in the form of a hypodermic needle and includes a tubular member or barrel 29 having a pointed end 30 for penetration of the skin and insertion into the body 26 and into a tumor 24 within the body as shown in FIG. 1. Barrel 29 has an internal circular bore 32 and an electrical conductor 34 is located concentrically within bore 32, and uniform spacing is maintained by a dielectric material 33, the conductor and dielectric material extending to the pointed end 30 as shown in FIG. 2. Antenna 20 comprises a transmission line for microwave energy from microwave generator 14 by way of coaxial cable 22. Lead 23 of cable 22 is coupled to conductor 34 and lead 25 is secured to barrel 29. The output end of antenna 20 is "open circuited" to allow incoming microwave energy to be broadcast or radiated in all directions from the antenna. The design of antenna 20 is such that there is impedance matching between the antenna and the human tissue in which the energy is radiated. By selecting the proper electromagnetic mode of operation, broadband frequency of operation in the antenna (transmission line) is readily achieved.

Typically, the diameter of barrel 29 is less than 16 gauge (0.065 inch O.D.). This gauge is chosen because the use of a hypodermic needle above this gauge is considered to be minimally invasive in the medical sense. The length of the needle typically is of a value sufficient to cause the needle to penetrate the skin and then penetrate a tumor so that the needle point 30 is substantially at the center of the tumor itself. Thus, the microwave energy radiated from the antenna will radiate in all directions and substantially uniformly heat the tumor so as to destroy the cancerous cells therein.

Microwave generator 14 can be of any desired construction. It can be a commercially available product, such as one made by Matsushita Electric Industries, Ltd. of Tokyo, Japan and identified as Magnetron 2M157. Such a microwave generator is rated at a frequency of 2450 MHz and 600 watts (continuous wave). This generator can be modified so as to produce lower power output levels such as 100 to 400 watts which is considered to be sufficient for the purposes to which the present invention is to be placed.

Microwave generator 14 typically is provided with an elapsed time clock 40 which times the delivery of output power applied to antenna 20 particularly after the tissue has reached a preset temperature. A keyboard 42 or other switching means is provided to permit the setting of operating times, depending upon the amount of microwave energy to be applied to a tumor by way of antenna 20. Typically, operating times of 20 minutes to 45 minutes are used, and a tumor is heated to a temperature in the rage of 43° to 46° C. for destroying cancerous cells in a tumor. Elapsed time at temperature is referred to as a dosage. Other operating times can be used, depending upon the condition of the tumor and the need for applying a greater or lesser dosage of heat thereto.

Temperature detector and control unit 16 is provided to detect temperatures at various locations around the outer periphery of a tumor as microwave energy is being imparted to the tumor by way of antenna 20. To this end, a plurality of temperature sensors 42 are inserted in body 56 at the outer periphery of tumor 24, and these sensors are coupled to respective leads 44 to a common lead 46 coupled with unit 16. When signals from sensors 42 are directed to unit 16, the signals are used to indicate relative temperature values at the outer periphery of the tumor. If the temperature determined by unit 16 approaches a maximum value, such as 46° C., the unit 16 actuates a switching network coupled with microwave generator 14, the switching network de-energizes microwave generator 14 for a period of time until the temperature at the outer periphery of the tumor is reduced to a certain value, such as 45° C. In this way, the heat energy necessary to kill cancer cells in a growth does not exceed a level which might possibly harm healthy cells in the region surrounding the tumor. Yet, once power is again applied to antenna 20, the antenna can radiate the energy so as to continue to heat the tumor for a time deemed necessary to kill the cancerous growth therein.

Suitable sensors for use in the present invention may be those made by Luxtron Corporation, Mountain View, Calif. and identified as Model 1000B biomedical thermometer.

Video system 18 is coupled by cable means 52 to video camera 27 which is to be used to insert the antenna 20 into a tumor 24 and to insert temperature sensors 42 into the body 26 at the outer periphery of the tumor. To this end, camera 27 is mounted on one side of the body 26 in alignment with tumor 24 therein. A strong light source 56 on the opposite side of tumor 24 directs light onto body 26. This will present an image capable of being sensed by camera 27, the image showing the presence of the tumor 24. This image in the form of video signals is directed to system 18 where it is displayed on monitor 21. Thus, a clinician, while viewing monitor 21, can insert antenna 20 into body 26 and then into tumor 24, so that the pointed end 30 of the antenna is substantially at the center of the tumor. Then, while viewing monitor 21, the clinician can insert the temperature sensors 42, one by one, so that the sensors will be at the outer periphery of the tumor for sensing the temperature immediately after heating of the tumor commences.

A video record can simultaneously be made with recorder 19 during the insertion of the antenna and sensors into the body. The record can also show the progress in the reduction of the size of the tumor. In this way, a permanent record of the procedure for a particular patient can be obtained and stored for future reference.

Generally, the presence or location of a tumor 24 in body 26 is determined by palpations; however, camera 27 and light source 56 can be used for the same purpose, if deemed desirable or necessary.

In operation, apparatus 10 is assembled as shown in FIG. 1. A person found to have a cancerous tumor, such as in the breast, is placed adjacent to camera 27 so that light 56 can illuminate the portion of the body containing the tumor. The camera then senses the image of the light passing through the body from light source 56 and this image will include a view of tumor 24. The image of the tumor will be displayed on monitor 21 and a continuous video record of the image can be obtained with recorder 19 while the camera is receiving light images from body 26.

With an image properly displayed on monitor 21, a clinician will then insert antenna 20 into body 26, the antenna being readily capable of penetrating the skin and entering tumor 24 because of the sharpened pointed end 30 of the needle-like construction of the antenna. The clinician will be able to determine, while viewing monitor 21, when the pointed end 30 of the antenna is substantially at the center of the tumor.

Following the placement of the antenna in the tumor, the clinician then inserts one or more sensors 42 into body 26 so that the sensor or sensors are at the outer periphery of the tumor. When the sensors are properly located, apparatus 10 is ready for the application of microwave energy to the antenna.

The clock-setting device 42 is then actuated to provide a specific operating time for operation of microwave generator 14. Then, the microwave generator is energized to cause microwave energy to be applied to antenna 20 which radiates the energy in substantially all directions throughout the tumor to heat the cells of the tumor. As the energy is applied, the temperature at the various locations on the periphery of the tumor are continuously sensed by sensors 42, and signals from these sensors are directed to unit 16 which monitors the magnitudes of the temperatures. If any one sensor senses a temperature above a predetermined maximum value, unit 16 will de-energize microwave generator 14, causing removal of power from antenna 20. This power interruption continues until the temperature at the outer periphery of the tumor once again drops to a pre-set value, whereupon power is once again restored to the antenna since unit 16 will again energize microwave generator 14 after the lower temperature is reached. This pattern of operation continues until the requisite amount of microwave energy has been applied for the preset time as determined by the setting on clock 40.

Apparatus 10 provides a means to develop and deliver microwave energy to a tumor in a simple and expeditious manner so as to provide an effective tool for the precise heating of a tumor with minimum discomfort to the patient. Apparatus 10 provides an integrated instrument characterized by reliability and simplicity of construction. The apparatus is especially suitable for treating tumors in the living breast, on or near the surface of the body and those locations that can be reached by the hypodermic needle antenna.

In the normal course of treatment of a tumor, if a tumor is detected, a physician can order a biopsy. Then, depending upon the results of the biopsy, the physician can select a course of treatment, such as surgery, chemotherapy, radiation therapy or combinations of these approaches. Apparatus 10 provides another option, namely, hyperthermia, which can be used alone or in combination with the other approaches.

If a physician prescribes hyperthermia, he will typically prescribe a temperature of about 44.5° C. and a duration of exposure at that temperature level, usually 20 to 40 minutes, as a function of the size of the tumor. Apparatus 10 will then be used to deliver enough microwave energy at a given frequency, such as 2450 MHz, an FCC approved frequency for medical applications, to elevate the tissue temperature to the prescribed level. However, other microwave frequencies may be selected as is determined by medical efficacy. Using this needle-like antenna eliminates the stray frequency broadcasting which would require RF shielding if other external transmission methods were used.

In FIG. 3, another antenna embodiment is shown. Antenna 20a has a pointed end formed by a conductor 34a which is longer than barrel 29a. The outer end of conductor 34a is pointed, and dielectric spacer material 33a is pointed between the outer end of barrel 29a and the outer end of conductor 34a.

Figure 5:
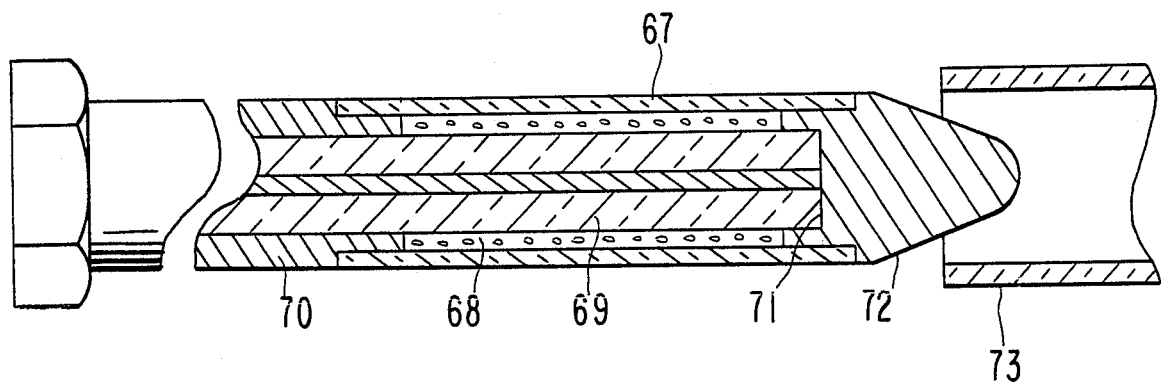
FIG. 5 is a cross-sectional view of an improved antenna of the present invention having impedance matching characteristics.

An antenna which can be used in the present invention as one shown FIG. 5 or hyperthermia application, typically in the treatment of tumors. The antenna shown in FIG. 5, broadly denoted by the numerical 50, is designed to solve the problem of impedance matching that exists when a coaxial cable is inserted into an air-filled plastic catheter that has been placed into human or animal tissue, such as a tumor which is about 80% water.

The impedance of prior art coaxial cable used in these applications is typically 50 ohms while air is approximately 377 ohms and moist tissues about 50 ohms. Without impedance matching, a mismatch occurs, causing a significant reflection of the microwave power in the opposite direction of propagation. This is detrimental to the application as the reflected power will be additive to the forward moving power and as a result, over-heating will occur in the cable and in the patient's tissue. Overheating can become significant enough to cause pain in the patient.

In the prior arts embodiment of FIG. 4, a coaxial cable 52 is inserted into a tubular catheter 54 placed in a mass 56 of human or animal tissue which is moist. The catheter is air filled and the direction of forward power propagation from the coaxial cable 52 is in the direction of arrow 58. Reflective power denoted by the arrow 60 is caused because of the mis-match in the impedance of the air in the space 62 surrounding the end 64 of the coaxial cable 52, such space 62 being within catheter 54 since the impedance of coaxial cable 52 and the tissue 56 is approximately 50 ohms and beacause the impedance of the air is approximately 377 ohms there is a mismatch which gives rise to a considerable amount of reflection denoted by the arrow 60 in the opposite direction of the desired propagation direction indicated by the arrow 62.

The purpose of antenna 50 (FIG. 5) is to significantly reduce or eliminate the air space 62 of the prior art embodiment of FIG. 4. This is accomplished in antenna's 50 by placing the concentric cable 50 thereof (FIG. 5) into a concentric plastic tube 67 that is sealed at both ends and is filled with an appropriate fluid, such as distilled water, denatured alcohol or an optimized molal solution of water and salt. By selecting the appropriate fluid for the diameters and thickness of tube 67, impedance matching is achieved and maximum forward transmission of the microwave energy is obtained. With the reflected power reduced to a few percent, transmission line heating is eliminated and patient comfort is assured.

As shown in FIG. 5, a space 68 surrounding the electrically non-conductive layer 69 of the antenna 50, space 68 being surrounded by tubing 67. Space 68 is filled with the appropriate fluid for impedance matching.

The rear end of tube 67 is sealed and press fitted in the forward, tubular end of a tubular member 70. The front end of tube 67 is press fitted on the rear boss 71 of an end plug 72.

Antenna 50 is terminated typically with a type SMA (male) connector or SMA (female) connector to assure compatability with a typical cable transmission lines from the source of microwave power. The male connector with its rotating collar allows the assembly to remain stationary during the connecting operation although this in itself is not a critical aspect.

End plug 72 is smooth and rounded to facilitate the insertion of the antenna into the catheter 73. The end plug also serves to center the coaxial cable within the concentric tubing, assuring optimum impedance matching characteristics. The outer diameter of the end plug is determined by the inner diameter of the catheter into which the end plug is to be inserted.

The length of the assembly from this from the SMA connector 75 to the end plug is not electrically important and will be set to be convenient to the user. A calibration may be added to assist in noting the depth of penetration of the assembly into the catheter which typically will have been previously inserted into the patient's tumor.

What is claimed is:

1. An antenna assembly for applying electromagnetic energy to a body part on or within a living body comprising:
   an antenna having a coaxial cable member adapted to be coupled with a source of electromagnetic power and to be inserted into the tissue of a body part on or within a living body, said member including a central, electrical conductive element and an outer, electrically non-conductive element surrounding the central element;
   a tube coupled with said member in surrounding, spaced relationship thereto, said tube having a pair of end plugs for forming with the tube a closed space surrounding the member and extending longitudinally thereof, one of the plugs having a pointed outer end; and
   a volume of fluid in said space, the impedance of the fluid being sufficient to match the impedance of the tissue with the impedance of the member.

2. An antenna as set forth in claim 1, wherein the fluid is selected from the group including water, alcohol and a mixture of water and salt.

3. An antenna as set forth in claim 1, wherein each end plug includes an electrically non-conductive plug.

* * * * *